United States Patent [19]

Pflueger et al.

[11] Patent Number: 5,326,342
[45] Date of Patent: Jul. 5, 1994

[54] ULTRASONIC ANGIOPLASTY DEVICE INCORPORATING ALL ULTRASOUND TRANSMISSION MEMBER MADE AT LEAST PARTIALLY FROM A SUPERLASTIC METAL ALLOY

[75] Inventors: Russell Pflueger, Newport Beach; Henry Nita, Lake Forest, both of Calif.

[73] Assignees: Baxter International Inc., Deerfield, Ill.; SonicStar International, Ltd., Jamestown, N.Y.

[21] Appl. No.: 910,478

[22] Filed: Jul. 8, 1992

Related U.S. Application Data

[62] Division of Ser. No. 640,190, Jan. 11, 1991, Pat. No. 5,304,115.

[51] Int. Cl.⁵ .............................................. A61B 17/20
[52] U.S. Cl. ........................................ 604/22; 607/97; 601/4
[58] Field of Search .................... 604/22; 128/24 AA; 606/128, 159, 169–171; 607/97

[56] References Cited

U.S. PATENT DOCUMENTS

| | | | |
|---|---|---|---|
| 3,565,062 | 2/1971 | Kuris | 606/159 |
| 3,823,717 | 7/1974 | Pohlman et al. | 128/24 AA |
| 4,188,952 | 2/1980 | Loschilov et al. | 606/79 |
| 4,665,906 | 5/1987 | Jervis | 606/78 |
| 4,692,139 | 9/1987 | Stiles | 604/22 |
| 4,808,153 | 2/1989 | Parisi | 606/159 |
| 4,870,953 | 10/1989 | DonMichael et al. | 606/159 |
| 4,924,863 | 5/1990 | Sterzer | 606/27 |
| 4,936,281 | 6/1990 | Stasz | 604/22 |
| 5,076,276 | 12/1991 | Sakurai et al. | 606/128 |
| 5,100,423 | 3/1992 | Fearnot | 606/45 |

FOREIGN PATENT DOCUMENTS

| | | | |
|---|---|---|---|
| 870579 | 10/1987 | PCT Int'l Appl. | 604/22 |
| 9001300 | 2/1990 | PCT Int'l Appl. | 604/22 |

*Primary Examiner*—C. Fred Rosenbaum
*Assistant Examiner*—Michael Rafa
*Attorney, Agent, or Firm*—Stetina & Brunda

[57] ABSTRACT

An ultrasonic angioplasty device comprising an elongate ultrasound transmission member having a proximal end attachable to an ultrasound generating device and a bulbous distal head or probe formed on the distal end thereof for effecting ablative treatment of an occluding lesion. The ultrasound transmission member may be formed of one or more superelastic metal alloys such as NiTi (50 at. % Ni). A guidewire lumen may be formed in the distal head or probe to permit passage of a guidewire therethrough. Portions of the ultrasound transmission member may be curved or bent. Portions of the ultrasound transmission member may be tapered or narrowed. One or more surface disruptions may be formed on the distal head or probe to improve treatment efficacy. An increased hardness coating or outer skin may be formed on the ultrasound transmission member. The device of the present invention may be incorporated into an angioscopic device.

7 Claims, 7 Drawing Sheets

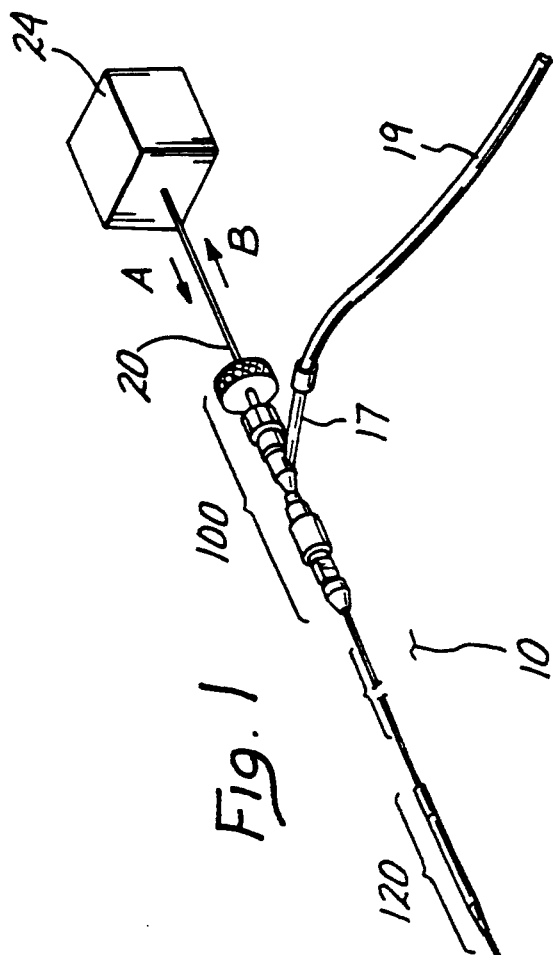
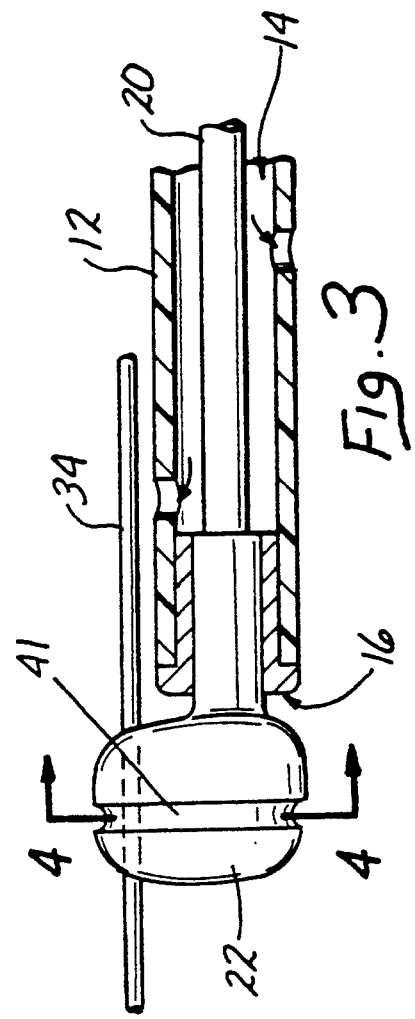
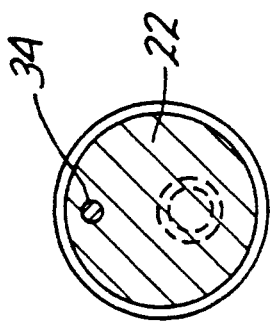

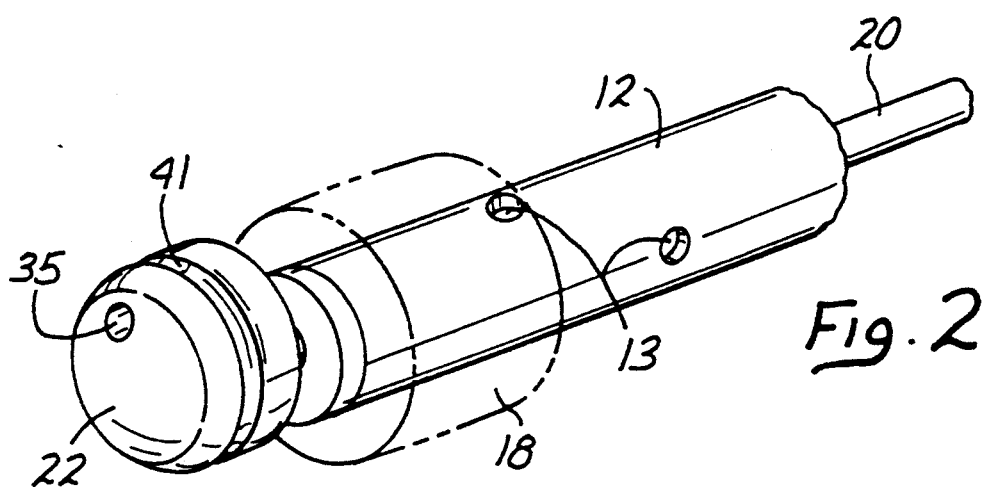
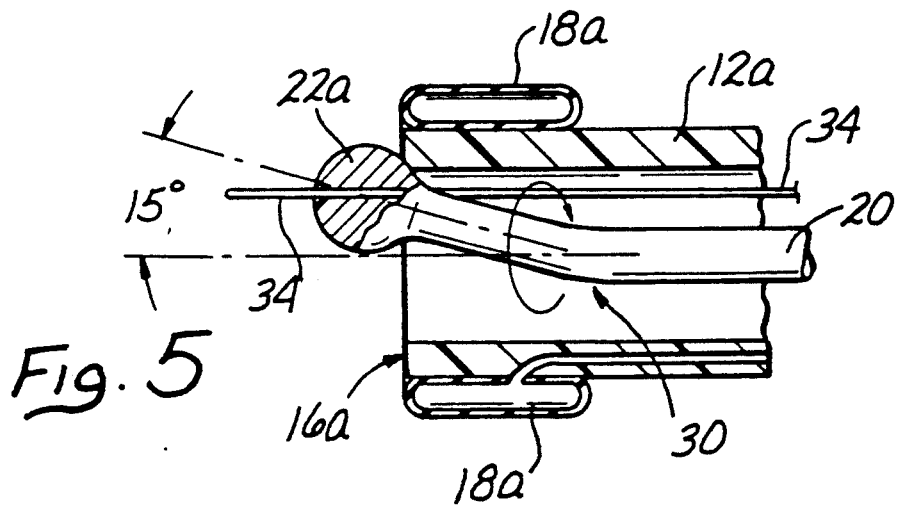
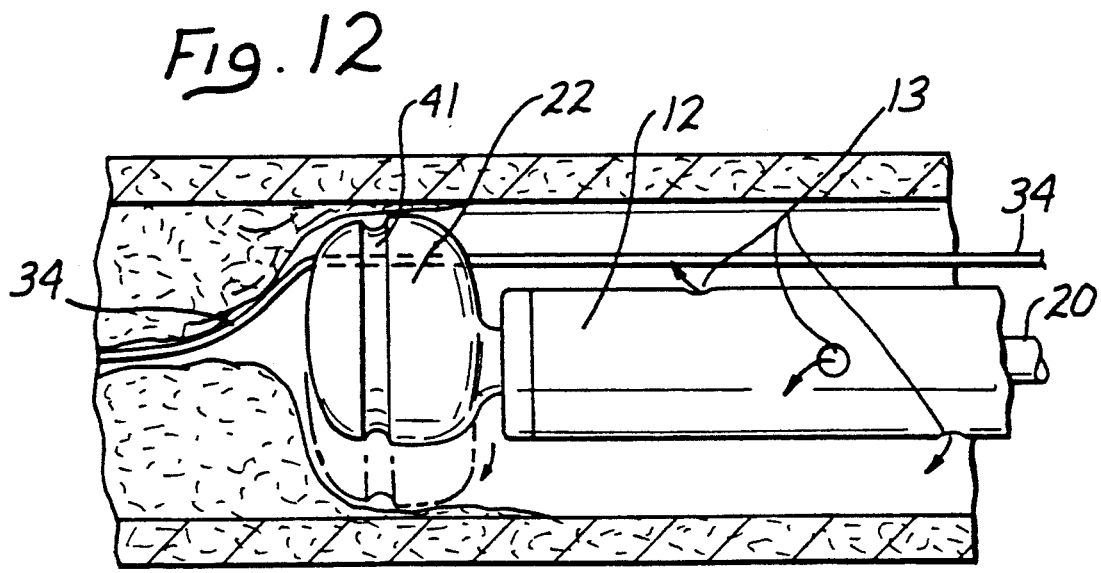

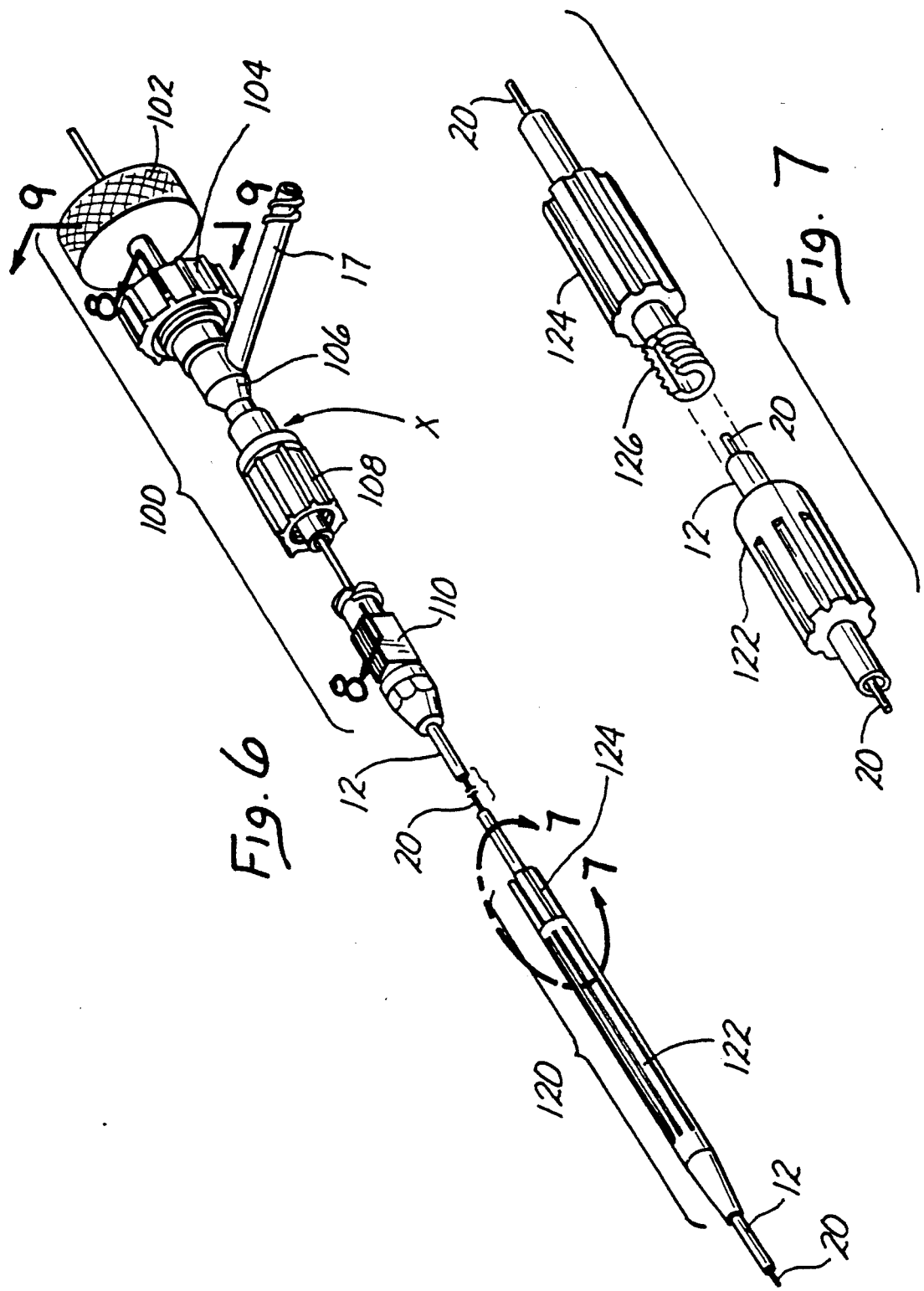

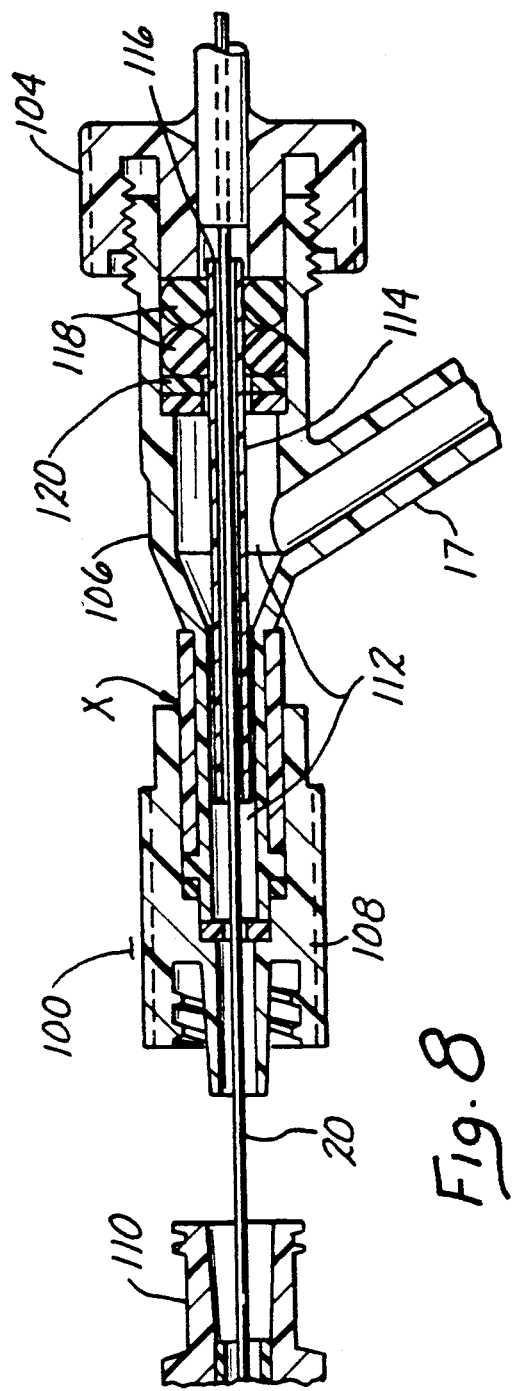
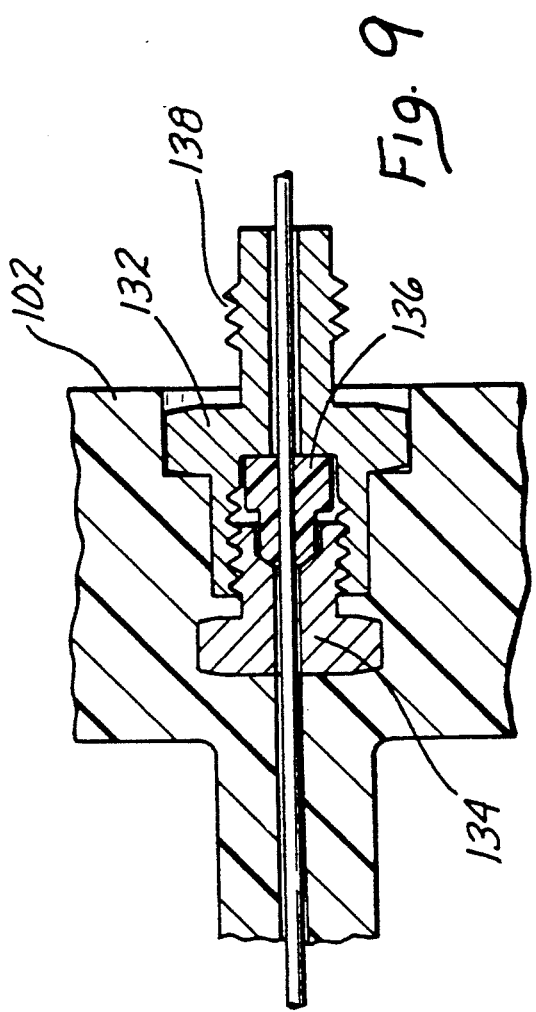

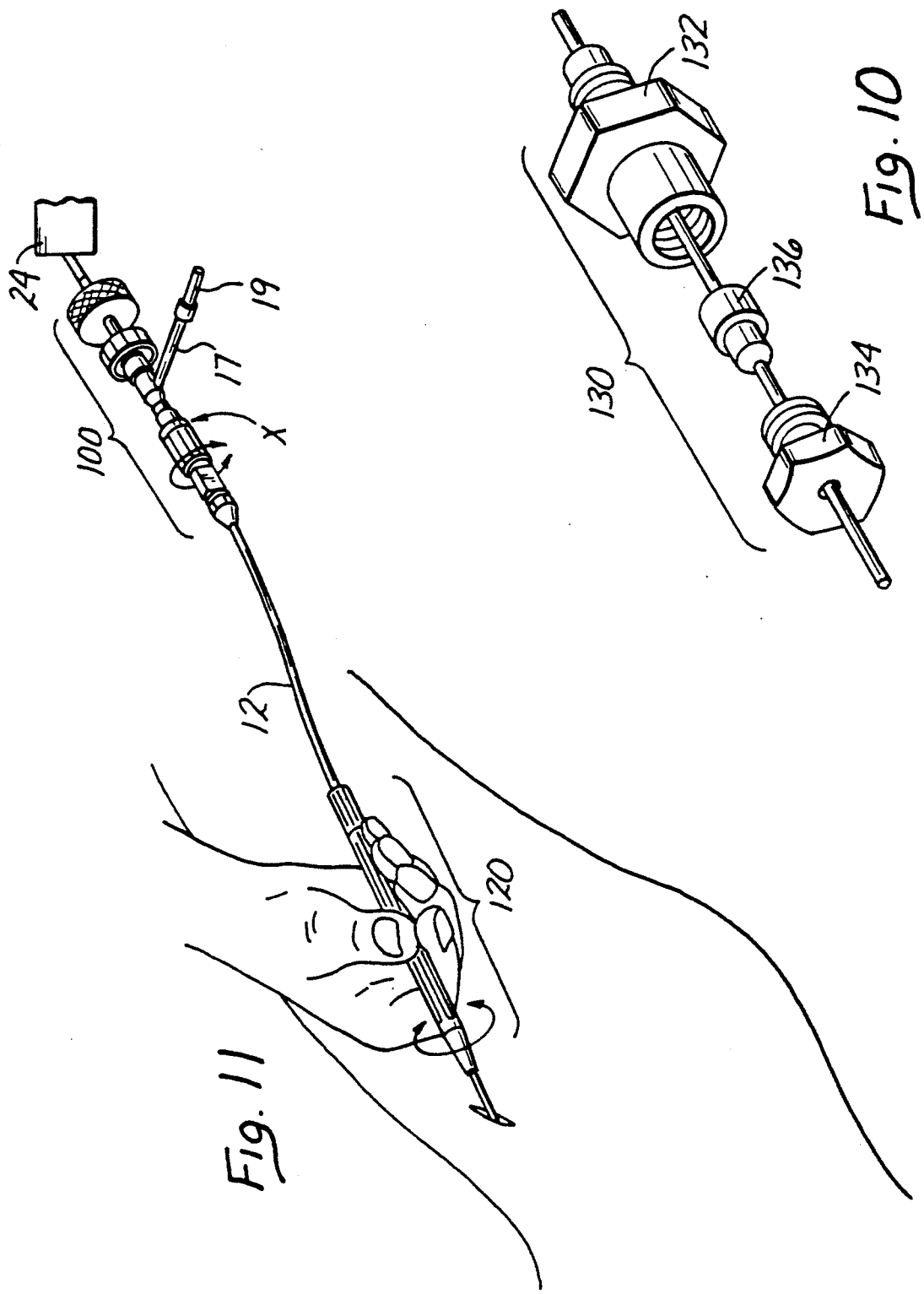

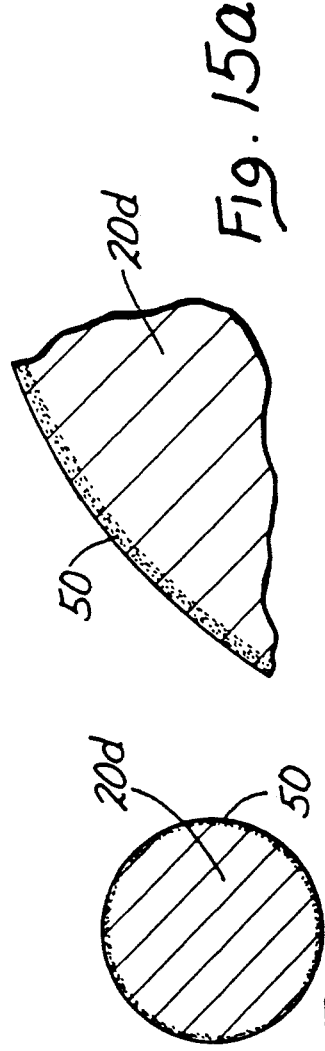
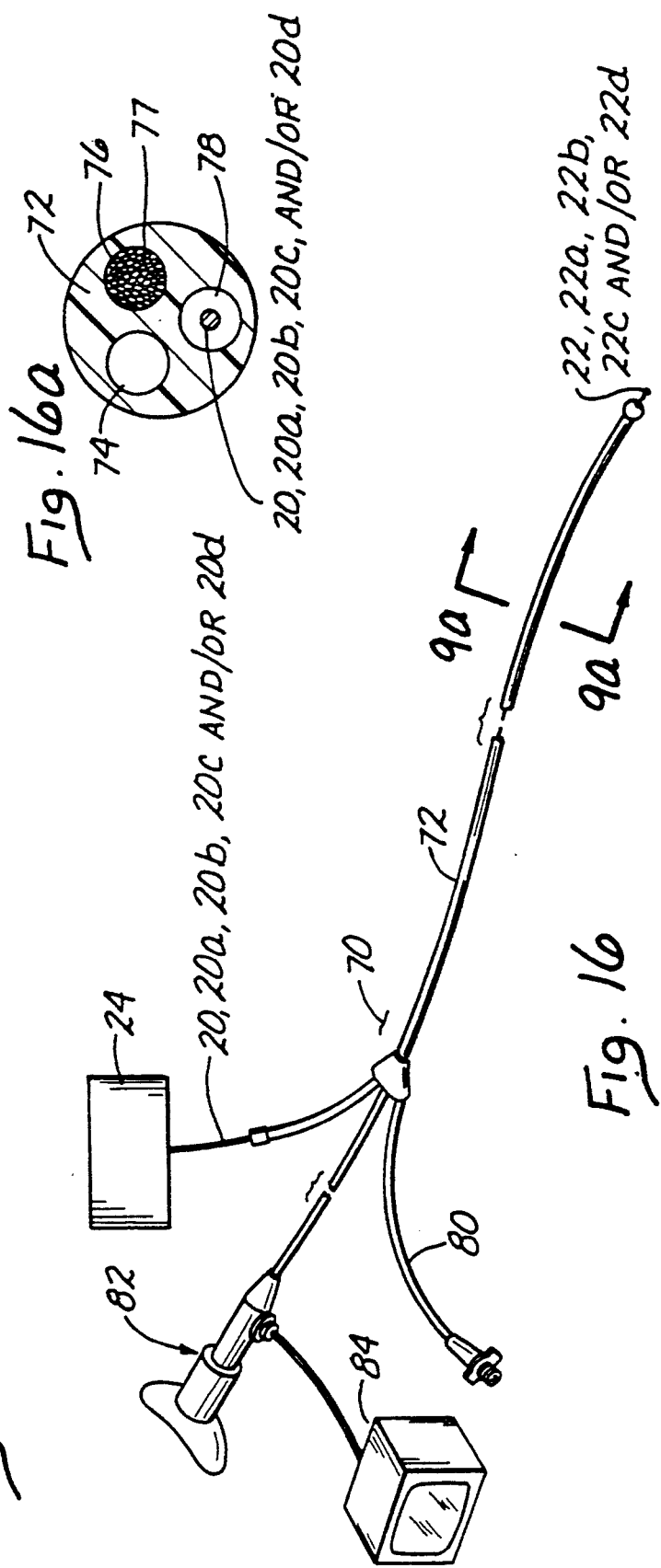

ULTRASONIC ANGIOPLASTY DEVICE INCORPORATING ALL ULTRASOUND TRANSMISSION MEMBER MADE AT LEAST PARTIALLY FROM A SUPERLASTIC METAL ALLOY

This is a division of application Ser. No. 07/640,190 filed on 11 Jan. 1991, now U.S. Pat. No. 5,304,115.

FIELD OF THE INVENTION

The present invention pertains to medical equipment and more particularly to an improved ultrasonic angioplasty catheter for effecting ultrasonic ablation of occlusive intravascular lesions.

BACKGROUND OF THE INVENTION

1. Angioplasty Procedures and Devices

In recent years, percutaneous transluminal angioplasty has become a commonly performed mode of treatment for various obstructive vascular disorders, including stenotic lesions of the coronary arteries, iliac arterial obstructions, femoral popliteal arterial obstructions, renal arterial obstructions, cerebrovascular arterial obstructions, coarctations of the aorta, stenotic arteries in transplant organs, stenotic saphenous vein bypass grafts, stenotic dialysis fistulas and stenotic portal systemic shunts.

To date, the most commonly used type of transluminal angioplasty procedure has been "balloon" angioplasty. Balloon angioplasty generally involves the positioning of a balloon catheter adjacent to or within the stenotic region of a blood vessel such that, upon inflation of the angioplasty balloon, the balloon will exert outward compressive force against the walls of the blood vessel thereby compressing the stenotic lesion and/or diametrically stretching the blood vessel. While such balloon angioplasty procedures have proven to be an efficacious and relatively safe means of treating some vaso-occlusive lesions, such balloon dilation procedures have proven less than optimal in the treatment of certain advanced lesions such as those consisting of fibrous or calcified atherosclerotic plaque. Moreover, by its very nature, the balloon angioplasty technique does not remove the occlusive lesion but, rather, simply compresses the lesion and/or dilates or stretches the surrounding blood vessel wall. There is a propensity for at least some balloon-treated lesions to subsequently reocclude some time after the balloon angioplasty procedure has been carried out. In some cases, full or partial re-occlusion of the blood vessel may result, thereby necessitating a repeat of the angioplasty procedure or other additional means of intervention (e.g. coronary artery bypass surgery).

Thus, it remains desirable to develop new alternatives to balloon dilation angioplasty procedures whereby the offending plaque or other stenotic lesion is actually removed, rather than merely stretched or compressed.

One viable alternative to the balloon dilation angioplasty technique is "ultrasonic" angioplasty. A number of methods and apparatus for ultrasonic angioplasty have been described in the prior art. One type of ultrasonic angioplasty apparatus known in the prior art comprises a flexible intravascular catheter having an ultrasound transmission wire (syn. "ultrasound transmission member") which extends longitudinally therethrough. The distal end of the ultrasound transmission wire is advanceable out of the distal end of the catheter. A bulbous distal head or probe is formed or mounted on the distal end of the ultrasound transmission wire. When ultrasonic energy is passed through the transmission wire, the distal head or probe will undergo vibratory movement in accordance with the sonic energy being transmitted therethrough. Such vibratory movement of the distal head or probe causes disintegration and ablation of the adjacent lesion, without damage to or perforation of the surrounding blood vessel wall.

Examples of ultrasonic angioplasty devices and related apparatus of the prior art include those described in U.S. Pat. Nos. 3,433,226 (Boyd), 3,823,717 (Pohlman et al.), 4,808,153 (Parisi), 4,936,281 (Stasz), 3,565,062 (Kuris), 4,924,863 (Sterzer), 4,870,953 (DonMichael et al.); and other Patent Publications WO87-05739 (Cooper), WO89-06515 (Bernstein et al.), WO90-0130, (Sonic Needle Corp.); EP 316,789 (DonMichael, et al.); DE 3,812,836 (Schubert) and DE 2,438,648 (Pohlman).

In particular, one prior art ultrasonic angioplasty device disclosed in U.S. Pat. No. 4,870,953 and European patent publication EP 31697 (DonMichael), is purported to effectively remove advanced fibrous or calcified atherosclerotic lesions as well as other thrombotic vascular occlusions. The device of U.S. Pat. No. 4,870,953 (DonMichael) comprises a flexible catheter having a wire like elongate ultrasound transmission member which extends longitudinally through the catheter. A bulbous distal head or probe is formed on the distal end of the ultrasound transmission member. The bulbous distal head may be alternately advanced out of and retracted into the distal end of the catheter. An ultrasound generation device is connected to the proximal end of the transmission member. When the ultrasound generation device is actuated, sound waves are passed through the transmission member, causing the bulbous distal head to undergo transverse and forward-/backward vibration. Such vibratory movement of the bulbous distal head allows the distal head, when positioned adjacent an atherosclerotic lesion, to break up and dissolve such atherosclerotic material in two (2) ways. First, it is purported that such vibratory movement of the distal head will effect direct "chipping" or "beating" of the occlusive material. Second, such vibratory movement of the distal head is purported to create turbulence or cavitation at the treatment site, such that said turbulence or cavitation will coact with and enhance the direct "chipping" or "beating" action of the distal head.

The entire disclosure and drawings of U.S. Pat. No. 4,870,953 (DonMichael, et al.) is expressly incorporated herein by reference.

One area in which the device of U.S. Pat. No. 4,870,953 (DonMichael et al.) and/or other prior art ultrasonic angioplasty devices may be subject to improvement is by improving the structural, physical and acoustical properties of the ultrasound transmitting member or wire which serves to transmit the sonic energy through the length of the catheter. While it remains desirable, that the ultrasound transmission member be endowed with sufficient flexibility and elasticity to navigate sharp bends and curves in the vascular anatomy, it is also the ultrasound transmission member or wire be of sufficient mass or thickness to transmit of the required amount of sonic energy therethrough. Additionally, it is desirable that the ultrasound transmission member or wire be sufficiently strong to prevent untoward breakage or fracture of the wire during use.

A second area in which the prior art ultrasonic angioplasty devices may be subject to improvement is in the configuration and design of the distal head and/or other portions of the ultrasound transmission member so as to optimize the therapeutic efficacy of the device in fragmenting and removing occlusive material from the surrounding artery walls.

2. Superelastic Materials

As will be described fully herein, one embodiment of the present invention incorporates and utilizes an ultrasound transmission member or wire formed of one or more material(s) which exhibit what is known as "superelasticity". The term "superelasticity", as used herein, shall generally mean the ability of a material to undergo large elastic deformations without the onset of plasticity or permanent deformation.

One particular group of metallic alloys, known as "shape memory alloys", are known to exhibit superelastic properties. Such shape memory alloys also demonstrate a "shape memory" phenomenon whereby the alloy is generally transformable, back and forth, between a low temperature configuration and a high temperature configuration. Transformation from the low temperature configuration to the high temperature configuration generally occurs as the alloy passes from its martensitic state to its austenitic state. Subsequent transformation from the high temperature configuration back to the low temperature configuration occurs as the alloy passes from its austenitic state to its martensitic state.

In addition to their unique ability to undergo temperature controlled changes in configuration, the shape memory alloys also exhibit temperature-dependent superelastic properties. The superelastic properties of the shape memory alloys are typically exhibited while the alloys remain in their martensitic states, but are lost as the alloys transition from their martensitic states to their austenitic states. Also, the degree or amount of superelasticity exhibited by a given shape memory alloy is generally dependent upon the stoichiometric ratio of the individual metal elements within that particular alloy.

Although one prior inventor has recognized that certain titanium alloys may exhibit better stress strain characteristics than those exhibited by high strength stainless steel or certain other metal alloys previously used for the transmission of sonic energy in ultrasound ablation devices (U.S. Pat. No. 4,920,954 and WO90-01300 (Alliger et al.), the prior art has heretofore failed to identify specific titanium or other metal alloys which provide the most suitable combination of a) strength, b) flexibility/elasticity and c) sound transmission properties for use in ultrasound ablation devices.

Accordingly, there remains a need in the art for the development of improved ultrasonic angioplasty devices, having ultrasound transmitting wires and/or ablation probes which are configurationally and/or materially modified to exhibit an improved combination of strength, flexibility/elasticity and sound transmitting characteristics, within the usual range of operating temperatures encountered in the ultrasonic angioplasty device.

SUMMARY OF THE INVENTION

The present invention overcomes some or all of the shortcomings of the prior art by providing an ultrasonic angioplasty device which comprises a flexible catheter body having at least one ultrasound transmission member or wire extending longitudinally therethrough. The ultrasound transmission member may be in a generally fixed position within the catheter such that the distal tip of the ultrasound transmission member extends just slightly beyond the distal tip of the catheter. Alternatively, the ultrasound transmission member may be slidably disposed within the catheter body such that the distal tip of the ultrasound transmission member may be alternately advanced beyond and retracted into the distal tip of the catheter. The enlarged or bulbous distal head may be formed on the distal tip of the ultrasound transmission member to enhance the ablative efficiency of the ultrasonic angioplasty device.

In accordance with the invention, the ultrasound transmission member or wire which extends longitudinally through the body of the catheter may be formed of one or more superelastic materials (e.g. "shape memory alloys") which exhibit superelasticity within a range of temperatures encountered by the ultrasound transmission member during use. One presently preferred shape memory alloy of which the ultrasound transmission member may be formed is a nickel-titanium alloy containing 50 atomic percent nickel.

In accordance with another aspect of the invention, the enlarged or bulbous distal head formed on the distal end of the ultrasound transmission member may be provided with a guidewire aperture or passageway extending therethrough to permit passage of a guidewire through the enlarged distal head.

In accordance with another aspect of the invention, a curve or bend may be formed near the distal end of the, ultrasound transmission member to cause the distal end thereof or distal head mounted thereon to be laterally displaced to one side, relative to the body of the ultrasound transmission member. Preferably, the curvature or bend in the ultrasound transmission member will form an angle of approximately 10°–45° and will be formed within approximately 3 cm of the distal end of the ultrasound transmission member.

In accordance with another aspect of the invention, the ultrasound transmission member may be narrowed or tapered near the distal end thereof. It is preferred that such narrowing or tapering be confined to a region within 5–30 cm of the distal tip of the ultrasound transmission member. It is preferable that the tapered or narrowed region cover the distal most 5–30 cm of the ultrasound transmission member.

In accordance with another aspect of the invention, the enlarged distal head or probe formed on the distal end of the ultrasound transmission member may be provided with one or more surface disruptions such as grooves, dimples, indentations, ridges, roughened areas or raised areas thereon to improve the ablative fragmentation of plaque or other material when the vibrating distal head comes in contact therewith.

One preferred coating which may be applied to the ultrasound transmission member is a titanium nitride (TIN) coating. Additionally, various surface plating techniques and/or compressive techniques may be utilized to form an increased density outer skin on the outer surface of the ultrasound transmission member or distal head.

In accordance with another aspect of the invention, the ultrasonic angioplasty device of the present invention incorporating some or all of the foregoing elements may be incorporated into an angioscopic device so as to be utilized in conjunction with fiber optic viewing equipment.

Further objects and advantages of the invention will become apparent to those skilled in the art upon reading an understanding of the following detailed description and the accompanying drawings.

BRIEF DESCRIPTION OF THE DRAWINGS

FIG. 1 is a perspective view of a first embodiment of an ultrasonic angioplasty catheter of the present invention.

FIG. 2 is an enlarged cutaway perspective view of the distal portion of a first embodiment of an ultrasonic angioplasty catheter of the present invention.

FIG. 3 is a longitudinal sectional view of the distal portion of a first embodiment of an ultrasonic angioplasty catheter of the present invention having a guidewire disposed thereon.

FIG. 4 is a cross-sectional view through line 4—4 of FIG. 3.

FIG. 5 is a longitudinal sectional view of the distal portion of an alternative second embodiment of an angioplasty catheter of the present invention.

FIG. 6 is a perspective view of a preferred proximal connection assembly which may be used in connection with the angioplasty catheter of the present invention.

FIG. 7 is an exploded perspective view of the portion of the device designated by line 7 of FIG. 6.

FIG. 8 is a longitudinal sectional view through line 8—8 of FIG. 6.

FIG. 9 is a longitudinal sectional view through line 9—9 of FIG. 6.

FIG. 10 is a perspective view of a preferred sonic connector assembly for gripping and connecting the ultrasonic transmission member of the device to an attendant ultrasound generator.

FIG. 11 is an operational illustration depicting the manner in which the ultrasonic angioplasty device of the present invention may be operated.

FIG. 12 is an operational illustration depicting the distal portion of an ultrasonic angioplasty device of the present invention disposed within a stenotic blood vessel.

FIG. 15 is a cross-sectional view of an ultrasound transmission member of the present invention having an outer coating or region of increased density formed on the outer surface thereof.

FIG. 15a is an enlarged view of a portion of FIG. 15.

FIG. 16 is a perspective view of an angioscope having (a) a first open irrigation/aspiration lumen, (b) a second optical fiber lumen wherein the optical fibers of the angioscope are disposed, and (c) a third ultrasound transmission member lumen wherein an ultrasound transmission member of the present invention is disposed.

DETAILED DESCRIPTION OF PREFERRED EMBODIMENTS

Figure 13A:
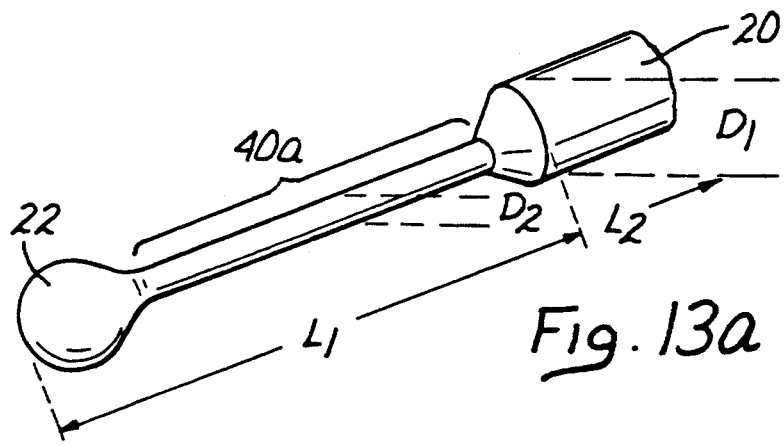
FIG. 13a is a perspective view of the distal head of an ultrasound transmission member of the present invention having a relatively sharp taper and narrow region formed just proximal to the distal head thereof.

The following detailed description and the accompanying drawings are provided for purposes of illustrating and describing specific embodiments of the present invention and are not intended to limit the scope of the present invention in any way.

The Angioplasty Device

In general, the angioplasty device of the present invention comprises a flexible elongate catheter body 12, 12a having at least one lumen 14, 14a extending longitudinally therethrough. An ultrasound transmission member or wire 20 extends longitudinally through the lumen 14, 14a of the catheter 12. A bulbous asymmetrical or symmetrical distal head 22, 22a, 22b, 22c, 22d, 22e is mounted on the distal end of the ultrasound transmission member 20 so as to be positionable beyond the distal tip 16, 16a of the catheter 12, 12a.

In one embodiment of the device shown in FIGS. 1-3, the bulbous distal head 22 comprises a bulbous or disc-shaped structure having an optional annular groove or surface disruption 41 extending around the outer surface thereof. The distal end of the ultrasound transmission member 20 is fused, attached or otherwise connected to the bulbous distal head 22 at a point which is off-center on the distal head 22, such that a greater portion of the bulbous distal head 22 will extend to one side of the catheter 12 than to the opposite side thereof. Such skewed or off-center positioning of the bulbous distal head 22 beyond one sidewall of the catheter is clearly illustrated in FIG. 3.

The bulbous distal head 22 may also be formed in various other bulbous ovoid or generally spherical shapes, including tear drop shapes, light bulb shapes, disc shapes and numerous others.

A plurality of fluid outflow ports 13 may be formed near the distal end 16, 16a of the catheter 12, 12a to permit fluid to flow in the distal direction through the lumen 14, 14a of the catheter and to pass outwardly from the distal end of the catheter through ports 13. The provision of such fluid outflow ports 13 near the distal tip of the catheter 12, 12a facilitates continual or intermittent passage of coolant liquid through the lumen 14, 14a in a manner which will continually or intermittently cool the ultrasound transmission member 20 by bathing its outer surface in coolant liquid. The passage of the coolant liquid over the ultrasound transmission member 20 will prevent the member 20 from overheating during use. This feature of the device 10 is particularly advantageous in embodiments wherein the ultrasound transmission member 20 is formed of a material having temperature dependent physical properties, such as the superelastic shape memory alloys hereinafter described which exhibit desirable superelastic properties only at temperatures below their martensite to austenite transition temperatures. In such embodiments, the temperature and/or flow rate of the coolant liquid may be adjusted and maintained so as to keep the temperature of the ultrasound transmission member 20 from rising above a predetermined temperature (e.g. its martensite to austenite transition temperature or other temperature at which the material will lose its desirable superelastic properties).

An optional balloon or inflatable cuff 18, 18a may be disposed about the distal portion of the catheter 12. Such balloon or cuff 18, 18a, when inflated will effectively occlude the surrounding blood vessel and hold the catheter 12 in a fixed position, as desired. In embodiments where the optional balloon or cuff 18, 18a is employed, the catheter 12 may incorporate a separate inflation fluid lumen 19 which extends longitudinally through the body of the catheter 12 and which terminates in a proximal port or connector to permit infusion/withdrawal of balloon inflation fluid to inflate and deflate the balloon 18, 18a.

A preferred proximal connection apparatus 100 is attached to the proximal end of the catheter 12 such that the ultrasound transmission member 20 may extend directly through the proximal connection apparatus such that it may be attached to an attendant ultrasound generator 24. As shown, the proximal connection apparatus may be in the form of a hollow body member having a hollow bore or inner chamber extending longitudinally through the proximal connector 100 and is fluidly connected to the inner lumen of side arm 17 such that cooled saline solution or other fluid may be infused through infusion tube 19, through side arm 17 and into the inner chamber formed within the proximal connection apparatus 100. Such coolant fluid will then flow distally into the lumen 14 of the catheter 12 and will continue in the distal direction through the lumen 14 of the catheter, thereby surrounding and bathing the ultrasound transmission member 20 as the fluid flows therealong. The coolant fluid will then flow out of fluid outflow lumens 13 formed near the distal end 16, 16a of the catheter 12, 12a.

As shown in FIGS. 6, 8 and 9, a preferred proximal connector assembly 100 comprises a proximal disc member 102, a rotatable coupling 104, a Y-fitting 106 having side arm 17 extending therefrom and a forward or frontal member 108 connectable to a catheter connection fitting 110. A generally hollow inner chamber 112 extends longitudinally through the connector assembly 100 such that the ultrasound transmission member 20 may pass directly therethrough, as shown in FIG. 8. A plastic tube made of material such as silicone is disposed around a portion of the ultrasound transmission member 20 within the inner chamber 112 of the connector assembly 100. As shown, it is preferred that the inner diameter of the plastic tube 114 be slightly larger than the outer diameter of the ultrasound transmission member 20 such that a space 116 exists therebetween. Dual O-rings 118 and a washer 120 formed of material such as plastic or silicone are disposed about the outer surface of the tube 114. It is preferable that the O-rings 118 and/or the washer 120 make direct contact with the outer surface of the tube 114 without exerting sufficient pressure to cause the tube 114 to collapse or compress inwardly as such inward compression may cause the tube 114 to come into contact with or press against the ultrasound transmission member 20 positioned therein. By such arrangement, the tube 114 is held firmly in place by the surrounding O-rings 118 and/or washer 120 while sufficient space 116 remains within tube 114 and around the ultrasound transmission member 20 to permit coolant fluid to flow from the inner chamber 112 through the space 116, thereby bathing and cooling the portion of the ultrasound transmission member 20 disposed within tube 114. Also, tube 114 is preferably sized, configured, positioned and made of material which is sufficiently rigid to dampen or limit side to side whipping or lateral movement of the ultrasound transmission member 20. Such limitation of the lateral or side to side movement of the ultrasound transmission member 20 by tube 114 will prevent the ultrasound transmission member 20 from striking the inner walls of the connector assembly 100 and will minimize undesirable side to side movement of the ultrasound transmission member 20 while permitting the desirable longitudinal (i.e. back and forth) vibration thereof.

An adjustable hand grip assembly 120 may be positioned on the catheter 12, 12a to facilitate operational twisting, turning and manipulation of the catheter 12 by the cardiologist or other practitioner. The use of the optional hand grip assembly 120 is particularly advantageous in embodiments where the preferred proximal connector 100 is also employed because the rotatable connector 104 incorporated in the assembly 100 facilitates rotation of the catheter 12 by the operator and, thus, the hand grip 120 is useful in that regard.

The optional, adjustable hand grip assembly 120 comprises a distal body 122 and a proximal gripping member 124. A concavity (not shown) is formed in the proximal end of the distal body 122 so as to receive the forward threaded portion 126 of the proximal locking member 124 therein. Such concavity is also tapered such that, as the forward threaded member 126 is screwed into the concavity, the taper of the concavity will compress the forward member 126 causing the split therein to close and causing the inner diameter of the forward member 126 to decrease, thereby gripping the surface of the catheter 12. By such arrangement, the proximal gripping member 124, when fully screwed into the concavity (not shown) on the proximal end of the distal body 122 will firmly grip the underlying catheter 12 and will hold the entire optional hand grip assembly 120 in a desired, fixed position on the catheter 12. Also, when the proximal gripping member 124 is dethreaded and removed from the concavity formed in the proximal end of the distal body 122, both the proximal gripping member 124 and the distal body 122 will be free to distally advance and retract proximally retract along the catheter 12, thereby providing for free adjustment of the position of the hand grip assembly 120 on the catheter 12.

A presently preferred sonic connector assembly 130 (FIG. 10) may be disposed on the proximal end of the ultrasound transmission member 20 and may be seated or housed within the disc member 102 as shown in FIG. 9. The presently preferred sonic connector assembly 130 comprises a proximal female portion 132, a distal male portion 134 and a compressible gripping ferrule disposed therebetween. The sonic connector assembly 130 may be seated within a depression or recess formed in the proximal disc member 102 as shown in FIG. 9. The gripping ferrule 136 is configured to seat within and be inwardly compressed by the concavity formed in the distal member 134 such that, when the distal member 134 and the proximal member 138 are threaded fully together, the ferrule will exert inward pressure on the ultrasound transmission member 20, thereby firmly gripping the ultrasound transmission member 20 and preventing slippage or rotation thereof.

Preferred Operation of the Basic Angioplasty Device

As illustrated in FIG. 11, the distal portion of the catheter 12, having the ultrasound transmission member 20 disposed therein is inserted percutaneously into an artery (e.g. femoral artery or brachial artery) and is advanced to a desired location such that the distal head 22 will be disposed adjacent, within or next to, an offending atherosclerotic lesion. As will be discussed more fully herein, a guidewire 34 may be employed in conjunction with the device to facilitate insertion and advancement of the device to its desired location. If a guidewire has been employed, such guidewire may be fully extracted and set aside after the angioplasty device has been fully inserted to its desired operational position.

The hand grip assembly 120 may be grippingly disposed at a desired location on the catheter 12 so as to enable the operator to conveniently grasp the catheter body 12 and to rotate the catheter about the rotational axis of coupling assembly 100.

With the bulbous distal head 22 disposed in its desired operative location, the ultrasound generator 24 is continually or paroxysmally operated to cause transmission of sonic energy through the ultrasound transmission member 20. Such transmission of sonic energy to the distal head 22 causes the distal head to undergo longitudinal and/or side to side vibratory movements. Such vibratory movement of the distal head 22 brings about minute fragmentation and ablation of the surrounding atherosclerotic lesion.

In some embodiments of the device, a rotational transducer may be employed so as to enable the operator to rotate the ultrasound transmission member 20 and distal head 22. This aspect of the invention is particularly applicable in embodiments wherein the distal head 22 is curved to one side or mounted off center so as to extend further to one side than the other. In such embodiments, the ability to rotate the distal head 22 will enable the distal head to optimally remove and ablate atherosclerotic plaque from the entire circumference of the blood vessel wall. Such action of the rotating distal head 22 is shown in FIG. 12.

As the ultrasonic angioplasty treatment continues, the operator may advance the ultrasound transmission member 20 and/or catheter 12 in a distal direction so as to cause the vibrating distal head 22 to ablate the offending lesion in its entirety.

During the procedure, chilled saline solution or other liquid may be infused through infusion tube 19, side arm 17 and distally through the lumen 14, 14a of the catheter 12, 12a so as to exit the catheter through distal liquid outflow ports 13. Such passage of cooling fluid through the catheter 12 will dissipate heat from the ultrasound transmission member 20.

Forming the Ultrasound Transmission Member of Superelastic Material(s)

In accordance with one aspect of the invention, all or a portion of the ultrasound transmission member may be formed of one or more materials which exhibit superelasticity. Such material(s) should preferably exhibit superelasticity consistently within the range of temperatures normally encountered by the ultrasound transmission member 20 during operation of the device 10.

Specifically, all or part of the ultrasound transmission member 20 may be formed of one or more metal alloys known as "shape memory alloys".

Examples of shape memory alloys which are usable to form the ultrasound transmission member 20 of the present invention are described in detail in U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions properties, chemistries and behavior of various memory alloys, any and all of which may be usable to form the superelastic ultrasound transmission member 20 of the present invention.

In particular, one presently preferred alloy of which the ultrasound transmission member 20 may be formed is a nickel-titanium alloy made up of 50.8 atomic percent nickel (NiT with 50.8 at. % Ni).

Because the shape memory alloys typically lose superelasticity as they transition from their martensite state to their austenite state, it is generally necessary that the particular shape memory alloy used to form the ultrasound transmission member 20 remains in its martensitic state during the ultrasonic angioplasty procedure, or at least during initial passage and movement of the ultrasonic angioplasty device through the sharp anatomical bends and curves of the vasculature. Because the transition from the martensite state to the austenite state generally occurs over a range of temperature, it is most desirable that the lowest temperature at which transition from the martensitic state to the austenitic state (known as $M_S$) be greater than the highest temperature at which the ultrasound transmission member 20 will be required to operate.

In view of the fact that it is desirable to maintain the shape memory alloy ultrasound transmission member 20 at a temperature below its martensite transition temperature ($M_S$), the present invention incorporates a flow through coolant system which enables the operator to pass a heat exchange fluid, such as chilled saline solution, through the catheter 12, 12a so as to bathe and flow over the surface of the ultrasound transmission member 20. To wit: cooled liquid may be infused through solution administration tube 19, through side arm 17, distally through catheter and out of outflow ports 13.

The temperature and flow rate of such coolant solution may be specifically controlled to insure that the ultrasound transmission member 20 will be maintained at a temperature below its martensite transition temperature ($M_S$), irrespective of which shape memory alloy the ultrasound transmission member 20 is formed or how much sonic energy is passed through the member 20. Also, to facilitate such control of the coolant solution, one or more thermocouples may be mounted within the catheter (and/or on the surface of the ultrasound transmission member 20) to permit continual electronic monitoring of the temperature of the ultrasound transmission member 20 so that automatic and/or manual alterations in the temperature and/or flow rate of the coolant solution may be effected as necessary to keep the member 20 below a desired maximum temperature (e.g. $M_S$).

Forming a Curve or Bend in the Ultrasound Transmission Member

In accordance with another aspect of the invention, the ultrasound transmission member 20a may be curved or bent near its distal tip, as shown in FIG. 5. This curve or bend near the distal tip of the ultrasound transmission member 20a will cause the distal head 22 of the ultrasound transmission member 20a to be laterally displaced to one side, relative to the body of the ultrasound transmission member 20a.

The ultrasound transducer 24 may be provided with a rotational capability so as to enable rotation of the ultrasound transmission member 20a in the manner indicated by the phantom lines and arrow X shown on FIG. 6. Such rotational maneuverability of the curved or offset distal head 22 may enable the distal head 22 to bend or whip farther in each lateral direction so as to come closer to the actual walls of the surrounding artery in cases where the straight unbent version 20 of the ultrasound transmission member is employed. Additionally, such bend in the distal portion of the ultrasound transmission member will facilitate guidance of the distal head into side vessels, branch vessels, and the like.

Preferably, the curvature or bend in the ultrasound transmission member 20a will form an angle of 10°–45°. Such 10°–45° bend or curvature may be accomplished gently or sharply. To wit: the 10°–45° bend or curvature may be formed 0.5 cm–3.0 cm over the length of the ultrasound transmission member 20a. Generally, the bend or curvature will be formed near the distal end of the ultrasound transmission member 20a and preferably within about 5 cm of the distal end thereof.

In the presently preferred embodiment shown in FIG. 5, the bend 30 is a simple 15° bend located 1 cm from the distal tip of the head 22 formed on the distal end of the ultrasound transmission member 28.

Forming a Guide Wire Passageway through the Distal Head or Probe

As shown in FIG. 5, the distal head 22a formed on either a straight 20 or curved 20a ultrasound transmission member may incorporate a guide wire passageway or aperture 32 to permit slidable advancement of a guide wire 34 therethrough.

As shown in FIG. 5, the guide wire aperture 35 may extend longitudinally through a portion of the distal head 22a such that the guide wire 34 may be positioned adjacent the length of the ultrasound transmission member 20 with the distal portion of the guide wire 34 being advanced through the guide wire passageway or aperture 35.

As shown in FIG. 2 one or both ends of the guide wire passageway or aperture 35 may incorporate an annular bevel or chamfered edge to facilitate passing of the guide wire 34 through the passageway or aperture 35, as seen in FIG. 5.

In use, the distal tip of the guide wire may be pre-inserted through the guide wire passageway or aperture 35 and, subsequently, the guide wire 34 and ultrasound transmission member 20, 20a may be advanced as a unit through the main lumen 14 of the catheter 12 to a point where the distal head 22a and/or the distal portion of the guide wire 34 are immediately adjacent to, or slightly beyond, the distal tip of the catheter 12. Thereafter, under radiographic guidance, the operator may selectively advance the guide wire 34 to break through an occlusive lesion or to gain access to a hard to reach vessel or area. After the guidewire has been selectively advanced to its desired location, the ultrasound transmission member 20, 20a and distal head 22a may be distally advanced along the guide wire to such desired location. Thereafter, the guide wire 34 may be retracted in a proximal direction so as to be fully withdrawn from the guide wire passageway or aperture 32. Further, the guide wire may, at that point, be completely extracted from the lumen 14 of the catheter by pulling the guide wire through the proximal opening 36. Such complete extraction of the guidewire will leave just the ultrasound transmission member 20 within the main lumen 14 of the catheter. After the guide wire has been fully or partially retracted in the manner described, the ultrasound generator 24 may be energized to send pulsative or continuous ultrasonic energy through the ultrasound transmission member 20. Such will result in concomitant longitudinal (forward-backward) and transverse (side to side) vibratory movement of the distal head 22a.

Additionally, in cases where, as described above, a bent or curved ultrasound transmission member 20a is employed, it may be desirable to fully or partially rotate such ultrasound transmission member 20 so as to cause the laterally displaced distal head 22a to migrate around the surrounding inner blood vessel wall, thereby reaching and ablating plaque which fully or partially surrounds such distal head 22a. Such rotation of a laterally displaced distal head 22a is illustrated in FIG. 4.

Tapering or Narrowing a Portion of the Ultrasound Transmission Member

In accordance with yet another aspect of the present invention the therapeutic efficacy of the device 10 may be improved by effecting certain alterations in the configuration of the distal head 22 and/or ultrasound transmission member 20.

Figure 13B:
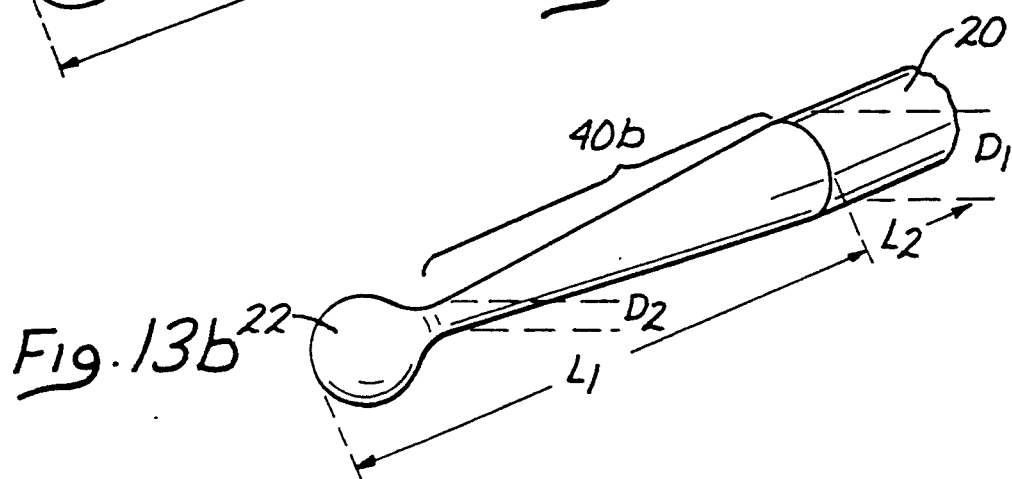
FIG. 13b is a perspective view of the distal head of an ultrasound transmission member of the present invention having a taper formed just proximal to the distal head thereof.

As shown in FIGS. 13a and 13b, one preferred modification to the ultrasound transmission member 20 comprises the incorporation of a tapered or narrowed region 40 at the distal end of the ultrasound transmission member 20, just proximal to the distal head 22. Such tapered or narrowed region 40 serves to enhance the flexibility of the ultrasound transmission member 20 at its distal end so as to enable the distal portion of the ultrasound transmission member 20 to traverse various bends in the blood vessels, without substantial narrowing of the overall diameter of the ultrasound transmission member 20 along the remainder of its length, thereby maintaining sufficient sonic energy transmission capability.

It is preferred that the tapered or narrowed region 40 of the ultrasound transmission member 20 be confined to an area within 5 to 30 cm of the distal tip of the distal head 22. By confining such tapered or narrowed region 40 to the distal end portion of the ultrasound transmission member 20, such does not result in any substantial narrowing or decrease in diameter of the remaining proximal portion of the ultrasound transmission member 20.

As shown the tapered or narrowed region 40 may comprise a gradual taper 40b (FIG. 13b), or a sharp taper with extended narrow region 40a (FIG. 13a) or any combination or hybrid form thereof.

When the ultrasound transmission member 20 is formed of titanium or one of the superelastic shape memory alloys described herein, it is preferable that the length $L_2$ of the ultrasound transmission member 20 lying proximal to the proximal most point on the tapered region 40 have a diameter D1 about 0.020"-0.030". Additionally, it is preferable that the length L1 from the distal tip of the distal head 22 to the proximal most point on the tapered region 40 be approximately 5 cm-30 cm and that the diameter D2 at the narrowest point of the narrowed or tapered region 40 be approximately 0.05"-0.020".

Forming One or More Surface Disruptions on the Distal Head or Probe

Separately or in conjunction with other aspects of the present invention as described herein, the configuration of the distal head 22 may be altered by the formation of one or more surface disruptions such as grooves, dimples, depressions, indentations, ridges, roughened areas or raised areas of the outer surface of the distal head 22. For example, a plurality of circumferential grooves, dimples, indentations, ridges, roughened areas or other depressed or raised areas may be formed in the outer surface of the distal head 22 to improve the ablative fragmentation of atherosclerotic plaque or other occlusive material accomplished by the vibratory movement of the distal head 22.

Examples of circumferential grooves which may be formed in the distal head 22 are shown in FIGS. 14, 14a, 14b, and 14c. As shown, one or more circumferential grooves 41a, 41b, 41c may be formed about the distal head 22b, 22c, 22d. Such circumferential grooves may be oriented in any direction and need not necessarily be oriented in the manner shown.

Figure 14:
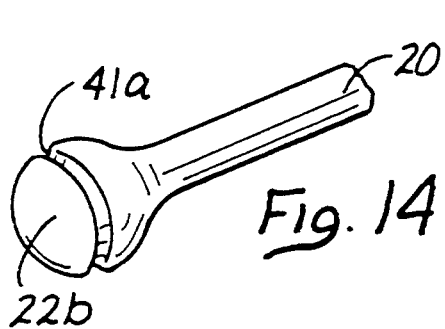
FIG. 14 is a perspective view of the distal head of an ultrasound transmission member of the present invention incorporating a circumferential groove formed about the distal head.
Figure 14A:
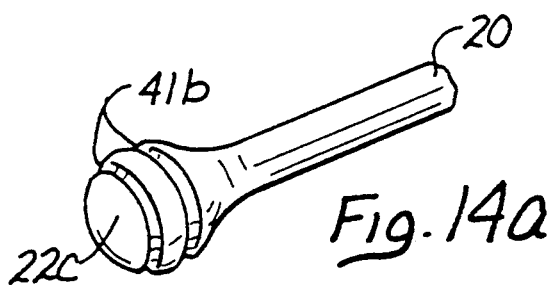
FIG. 14a is a perspective view of the distal head of an ultrasound transmission member of the present invention incorporating two circumferential grooves formed about the distal head.
Figure 14B:
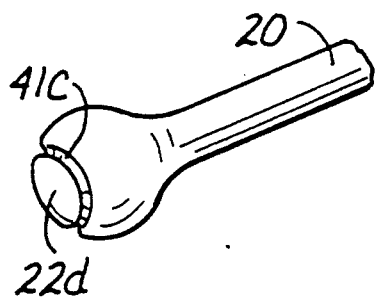
FIG. 14b is a perspective view of the distal head of an ultrasound transmission member of the present invention incorporating an alternate circumferential groove formed about the distal head.
Figure 14C:
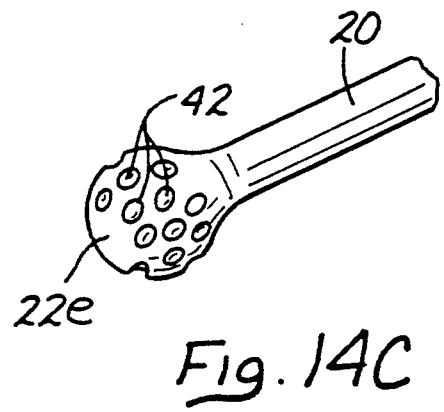
FIG. 14c is a perspective view of the distal head of an ultrasound transmission member of the present invention incorporating a multiplicity of indentations formed in the distal head.

An example of surface disruptions in the form of dimples or indentations 42 which may be formed in the surface of the distal head 22e is shown in FIG. 14c.

The formation of surface disruptions such as grooves 41a, 41b or 41c, dimples 42, indentations, ridges, roughened areas, raised areas, bumps or ribs formed in or on the outer surface of the distal head will, depending on the specific spacing and/or configuration of such surface disruptions(s), serve to enhance the fragmentation and ablation of the lesion or occluding matter with which the distal head 22b, 22c, 22d comes in contact while undergoing sonic vibration.

Forming a Coating or Skin on the Ultrasound Transmission Member and/or the Distal Head Separately or in conjunction with other aspects of the invention as described herein, a coating or relatively hard outer skin may be applied to lower the coefficient of friction and/or increase the surface hardness of all or a portion of the ultrasound transmission member 20, 20a, 20b, 20c and/or the distal head 22, 22a, 22b, 22c, 22d. The provision of such coating or outer skin serves to reduce the chances of fracturing during high cycle fatigue as may occur with uncoated titanium or aluminum ultrasound transmission members.

One particular coating which is effective in the present invention is a titanium nitride coating marketed under the designation SCI-8 by Multi-Arch Scientific Coatings, 200 Round Hill Drive, Rockaway, N.J. 07866. Such SCI-8 titanium nitride coating has a Rockwell hardness of approximately 80 Rc.

In embodiments of this invention wherein the ultrasound transmission member 20, 20a, 20b, 20c and/or the distal head 22, 22a, 22b, 22c, 22d are formed of superelastic metal alloys, the chemical constituency or formulation of the increased-hardness coating may be adjusted and/or selected to achieve desired coating adhesion to such underlying alloy material(s).

The coatings which may be applied in accordance with this aspect of the invention are not limited to the above-described titanium nitride (TIN) coating. In fact, any types of coatings which exhibit the desired degree of hardness and appropriate biological compatibility may be used.

It is preferable that the coatings employed for this purpose, when fully cured, will exhibit a surface hardness which is greater than the material (e.g. titanium, aluminum, titanium alloy, other superelastic alloy, etc.) of which the underlying ultrasound transmission member 20, 20a, 20b, 20c and/or distal head 22, 22a, 22b, 22c, 22d is formed.

As an alternative to the application of a surface coating to increase surface hardness, the same or similar increase in surface hardness may be achieved, in accordance with this aspect of the invention, by various surface plating techniques and/or compression of the outer surface of the ultrasound transmission member 20, 20a, 20b, 20c and/or the distal head 22, 22a, 22b, 22c, 22d by peaning, ion impregnation, rotary swaging or other techniques which provide for the formation of an increased density or increased hardness outer layer, coating or skin on the outer surface of the ultrasound transmission member or distal head.

One process which may be employed for lowering the coefficient of friction and/or increasing the surface hardness of the ultrasound transmission member 20 is that known as the Tiozide ™ process (Tiozide Co., Inc., Huntington Beach, Calif.). The Tiozide ™ comprises an electrolytic conversion hard coating of titanium using an all alkaline bath.

It is preferable that, in accordance with this aspect of the invention, the hardness of the outer coating or skin formed on the ultrasound transmission member 20 and/or the distal head 22, 22a, 22b, 22c, 22d provide an increase of at least 50 c Rockwell over the hardness of the underlying material of which the ultrasound transmission member and/or distal head is made and preferably an increase of such hardness of about 60-65 c Rockwell as defined by *Machinery's Handbook* 2d Ed., Editors E. Oberg, F. Jones and H. Horton (Industrial Press Inc. 1986) pp. 2126-2133.

As illustrated in FIGS. 15 and 15a, the outer coating or skin 50 will preferably fully surround and encase the shaft of the ultrasound transmission member 20d.

Incorporating of the Ultrasonic Angioplasty Device into an Angioscopic Device

Further in accordance with the present invention, any or all of the foregoing elements of this invention may be incorporated into an angioscopic device so as to provide for visual transluminal monitoring of the ultrasonic angioplasty procedure. As shown in FIGS. 16 and 16a, an angioscope 70 of the present invention may comprise a flexible catheter body 72 having a first lumen 74, a second lumen 76 and a third lumen 78 extending longitudinally therethrough. The first lumen 74 comprises an open fluid infusion/aspiration lumen which terminates proximally in infusion/aspiration side arm 80. The second lumen 76 contains a plurality of optical fibers extending longitudinally therethrough and providing optical image transmission to the angioscopic device 82 mounted on the proximal end thereof. An attendant TV monitor 84 is provided for optimal viewing of the procedure. The optical fibers 77 within second lumen 76 may comprise light transmitting fibers which function to transmit light from a proximal light source to the distal tip of the catheter 72 and image return fibers which serve to transmit the optical image from the distal tip of the catheter 72 to the angioscopy device 82.

The third lumen 78 contains one of the ultrasound transmission members 20 of the present invention. A bulbous distal head 22, 22a, 22b, 22c, 22d of the present invention will be continuous with, formed on or attached to the distal end thereof.

Thus, the angioscopic embodiment shown in FIGS. 16 and 16a may incorporate the basic angioplasty device of the present invention including one or more of the above-described improvements thereto in any possible combinations thereof.

The invention has been described herein with particular reference to presently preferred embodiments of the invention. It will be appreciated by those skilled in the art that various additions, alterations, modifications and deletions may be made to the above-described embodiments without departing from the spirit and scope of the present invention. Thus, it is intended that all such additions, alterations, modifications and deletions be included within the scope of the appended claims and the equivalence thereof.

What is claimed is:

1. An ultrasound transmitting catheter device for transmitting ultrasonic energy from an extrocorporeal ultrasound generating apparatus to a location within a mammalian body, said catheter device comprising:
   an elongate flexible catheter having a proximal end, a distal end and at last one lumen extending longitudinally therethrough; and
   an ultrasound transmission member formed of a superelastic metal alloy and having a proximal end which is connectable to an ultrasound source and a distal end which is substantially coterminous with the distal end of said catheter body; and
   said ultrasound transmission member extending longitudinally through said flexible catheter such that, when said flexible catheter is placed in a bent configuration, said ultrasound transmission member will concomitantly assume a bent configuration.

2. The device of claim 1 wherein said ultrasound transmission member is formed of nickel-titanium alloy.

3. The device of claim 1 wherein said ultrasound transmission member is formed of nickel-titanium alloy having a nickel content of approximately 50.8 atomic percent.

4. The device of claim 1 further comprising:
   at least one coolant inlet port located near the proximal end of the catheter for infusion of a coolant liquid into the lumen of the catheter; and
   at least one coolant outlet aperture formed near the distal end of said catheter to allow coolant liquid to flow out of the lumen of said catheter.

5. The device of claim 1 wherein said ultrasound transmission member is held in a substantially fixed longitudinal position relative to said catheter.

6. The device of claim 1 wherein said superelastic metal alloy is a metal alloy which exhibits superelastic properties at temperature below its martensite transition temperature.

7. The device of claim 4 wherein said superelastic metal alloy exhibits superelastic properties at temperatures below its martensite transition temperature and wherein said coolant inlet and outlet aperture are sized and configured to permit sufficient coolant flow through said catheter to maintain said superelastic ultrasound transmission member at a temperature below its martensite transition temperature during use.

* * * * *